(12) United States Patent
Wolf et al.

(10) Patent No.: US 10,878,966 B2
(45) Date of Patent: Dec. 29, 2020

(54) SYSTEM AND METHOD FOR ANALYSIS AND PRESENTATION OF SURGICAL PROCEDURE VIDEOS

(71) Applicant: Theator, Inc., San Mateo, CA (US)

(72) Inventors: Tamir Wolf, New York City, NY (US); Dotan Asselmann, Tel Aviv (IL)

(73) Assignee: THEATOR INC., San Mateo, CA (US)

( * ) Notice: Subject to any disclaimer, the term of this patent is extended or adjusted under 35 U.S.C. 154(b) by 0 days.

(21) Appl. No.: 16/101,543

(22) Filed: Aug. 13, 2018

(65) Prior Publication Data

US 2018/0366231 A1    Dec. 20, 2018

Related U.S. Application Data

(60) Provisional application No. 62/544,834, filed on Aug. 13, 2017, provisional application No. 62/667,847, filed on May 7, 2018.

(51) Int. Cl.

| | |
|---|---|
| *G16H 70/20* | (2018.01) |
| *G06F 3/0482* | (2013.01) |
| *G06K 9/00* | (2006.01) |
| *G06T 7/00* | (2017.01) |
| *G16H 10/60* | (2018.01) |
| *G06K 9/32* | (2006.01) |
| *G16H 30/20* | (2018.01) |
| *G16H 40/63* | (2018.01) |
| *G16H 20/40* | (2018.01) |
| *G16H 30/40* | (2018.01) |

(Continued)

(52) U.S. Cl.
CPC ............ *G16H 70/20* (2018.01); *G06F 3/0482* (2013.01); *G06K 9/00711* (2013.01); *G06K 9/3233* (2013.01); *G06T 7/0012* (2013.01); *G16H 10/60* (2018.01); *G16H 20/40* (2018.01); *G16H 30/20* (2018.01); *G16H 30/40* (2018.01); *G16H 40/63* (2018.01); *G16H 50/70* (2018.01); *G06F 40/20* (2020.01); *G06K 2009/00738* (2013.01); *G06K 2209/05* (2013.01); *G06T 2207/10016* (2013.01)

(58) Field of Classification Search
CPC . G06F 3/0482; G06T 7/0012; G06K 9/00711; G06K 2009/00738; G06K 2209/05
See application file for complete search history.

(56) References Cited

U.S. PATENT DOCUMENTS

2007/0238981 A1* 10/2007 Zhu ................ A61B 90/36
                                        600/424
2014/0297301 A1* 10/2014 Rock .................. G06Q 10/103
                                        705/2

(Continued)

*Primary Examiner* — Seth A Silverman
(74) *Attorney, Agent, or Firm* — Finnegan, Henderson, Farabow, Garrett & Dunner, LLP

(57) ABSTRACT

Systems and methods for analysis and presentation of videos of surgical procedures are provided. For example, a video of a surgical procedure may be obtained, time points corresponding to key intraoperative events may be obtained, and properties of the key intraoperative events may be obtained. Further, the properties of the key intraoperative events may be presented to a user, and a selection of a selected intraoperative event may be received from the user. In response, part of the video associated with the time point corresponding to the selected intraoperative event may be presented.

23 Claims, 9 Drawing Sheets

(51) Int. Cl.
*G16H 50/70* (2018.01)
*G06F 40/20* (2020.01)

(56) References Cited

U.S. PATENT DOCUMENTS

| | | | |
|---|---|---|---|
| 2016/0067007 A1* | 3/2016 | Piron | A61B 5/7246 |
| | | | 705/3 |
| 2016/0259888 A1* | 9/2016 | Liu | G06F 19/321 |
| 2017/0119258 A1* | 5/2017 | Kotanko | G06T 7/254 |
| 2018/0322949 A1* | 11/2018 | Mohr | G16H 30/40 |

* cited by examiner

SYSTEM AND METHOD FOR ANALYSIS AND PRESENTATION OF SURGICAL PROCEDURE VIDEOS

CROSS REFERENCES TO RELATED APPLICATIONS

This application claims the benefit of priority of U.S. Provisional Patent Application No. 62/544,834, filed on Aug. 13, 2017, and U.S. Provisional Patent Application No. 62/667,847, filed on May 7, 2018.

BACKGROUND

Technological Field

The disclosed embodiments generally relate to systems and methods for analysis and presentation of documentation of surgical procedures. More particularly, the disclosed embodiments relate to systems and methods for analysis and presentation of videos of surgical procedures.

Background Information

Audio sensors are now part of numerous devices, and the availability of audio data produced by those devices is increasing.

Image sensors are now part of numerous devices, and the availability of images and videos produced by those devices is increasing.

Video documentation of surgical procedures is becoming more and more prevalent.

SUMMARY

In some embodiments, systems and methods for analysis and presentation of videos of surgical procedures are provided. For example, a video of a surgical procedure may be obtained, time points corresponding to key intraoperative events may be obtained, and properties of the key intraoperative events may be obtained. Further, the properties of the key intraoperative events may be presented to a user, and a selection of a selected intraoperative event may be received from the user. In response, part of the video associated with the time point corresponding to the selected intraoperative event may be presented.

DESCRIPTION

Figure 1A:
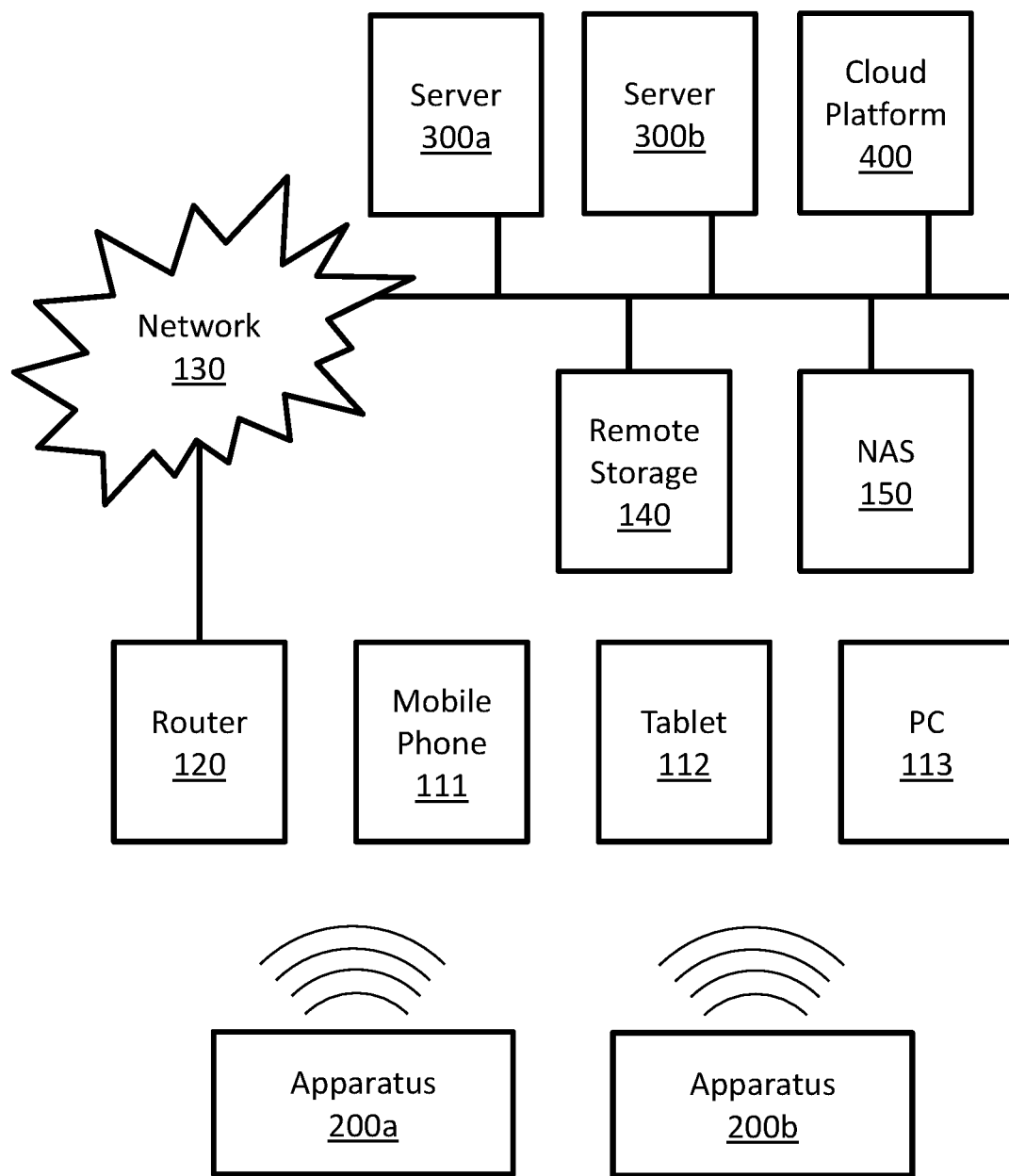
FIGS. 1A and 1B are block diagrams illustrating some possible implementations of a communicating system.

Unless specifically stated otherwise, as apparent from the following discussions, it is appreciated that throughout the specification discussions utilizing terms such as "processing", "calculating", "computing", "determining", "generating", "setting", "configuring", "selecting", "defining", "applying", "obtaining", "monitoring", "providing", "identifying", "segmenting", "classifying", "analyzing", "associating", "extracting", "storing", "receiving", "transmitting", or the like, include action and/or processes of a computer that manipulate and/or transform data into other data, said data represented as physical quantities, for example such as electronic quantities, and/or said data representing the physical objects. The terms "computer", "processor", "controller", "processing unit", "computing unit", and " processing module" should be expansively construed to cover any kind of electronic device, component or unit with data processing capabilities, including, by way of non-limiting example, a personal computer, a wearable computer, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) may be included in at least one embodiment of the presently disclosed subject matter. Thus the appearance of the phrase "one case", "some cases", "other cases" or variants thereof does not necessarily refer to the same embodiment(s). As used herein, the term "and/or" includes any and all combinations of one or more of the associated listed items.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

It should be noted that some examples of the presently disclosed subject matter are not limited in application to the details of construction and the arrangement of the components set forth in the following description or illustrated in the drawings. The invention can be capable of other embodiments or of being practiced or carried out in various ways.

Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

FIG. 1A is a block diagram illustrating a possible implementation of a communicating system. In this example, apparatuses 200a and 200b may communicate with server 300a, with server 300b, with cloud platform 400, with each other, and so forth. Possible implementations of apparatuses 200a and 200b may include apparatus 200 as described in FIGS. 2A and 2B. Possible implementations of servers 300a and 300b may include server 300 as described in FIG. 3. Some possible implementations of cloud platform 400 are described in FIGS. 4A, 4B and 5. In this example apparatuses 200a and 200b may communicate directly with mobile phone 111, tablet 112, and personal computer (PC) 113. Apparatuses 200a and 200b may communicate with local router 120 directly, and/or through at least one of mobile phone 111, tablet 112, and personal computer (PC) 113. In this example, local router 120 may be connected with a communication network 130. Examples of communication network 130 may include the Internet, phone networks, cellular networks, satellite communication networks, private communication networks, virtual private networks (VPN), and so forth. Apparatuses 200a and 200b may connect to communication network 130 through local router 120 and/or directly. Apparatuses 200a and 200b may communicate with other devices, such as servers 300a, server 300b, cloud platform 400, remote storage 140 and network attached storage (NAS) 150, through communication network 130 and/or directly.

Figure 1B:
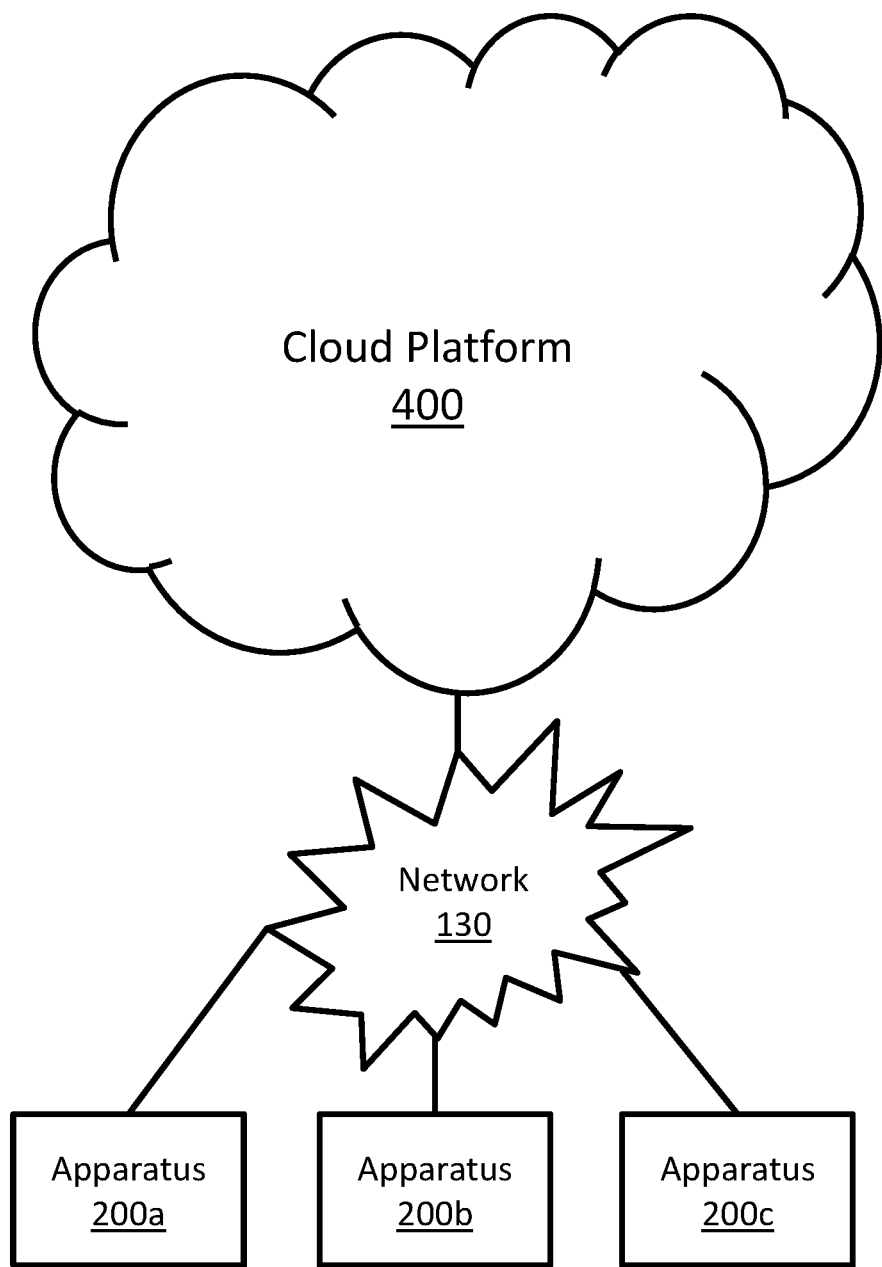

FIG. 1B is a block diagram illustrating a possible implementation of a communicating system. In this example, apparatuses 200a, 200b and 200c may communicate with cloud platform 400 and/or with each other through communication network 130. Possible implementations of apparatuses 200a, 200b and 200c may include apparatus 200 as described in FIGS. 2A and 2B. Some possible implementations of cloud platform 400 are described in FIGS. 4A, 4B and 5.

FIGS. 1A and 1B illustrate some possible implementations of a communication system. In some embodiments, other communication systems that enable communication between apparatus 200 and server 300 may be used. In some embodiments, other communication systems that enable communication between apparatus 200 and cloud platform 400 may be used. In some embodiments, other communication systems that enable communication among a plurality of apparatuses 200 may be used.

Figure 2A:
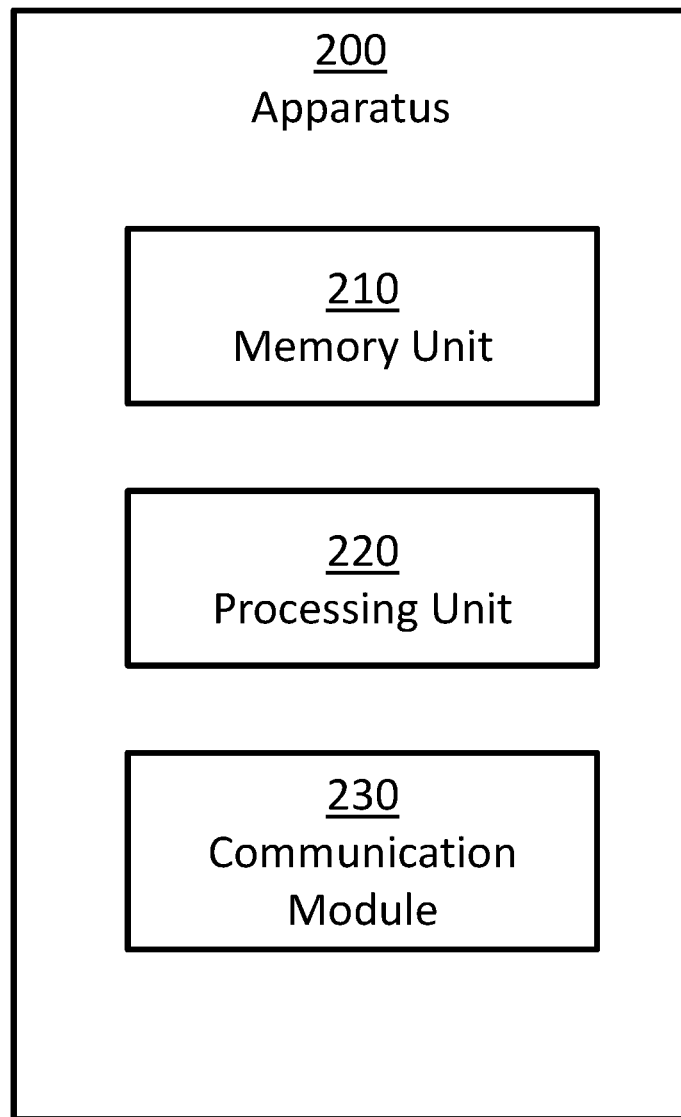
FIGS. 2A and 2B are block diagrams illustrating some possible implementations of an apparatus.

FIGS. 2A is a block diagram illustrating a possible implementation of apparatus 200. In this example, apparatus 200 may comprise: one or more memory units 210, one or more processing units 220, and one or more communication modules 230. In some implementations, apparatus 200 may comprise additional components, while some components listed above may be excluded.

Figure 2B:
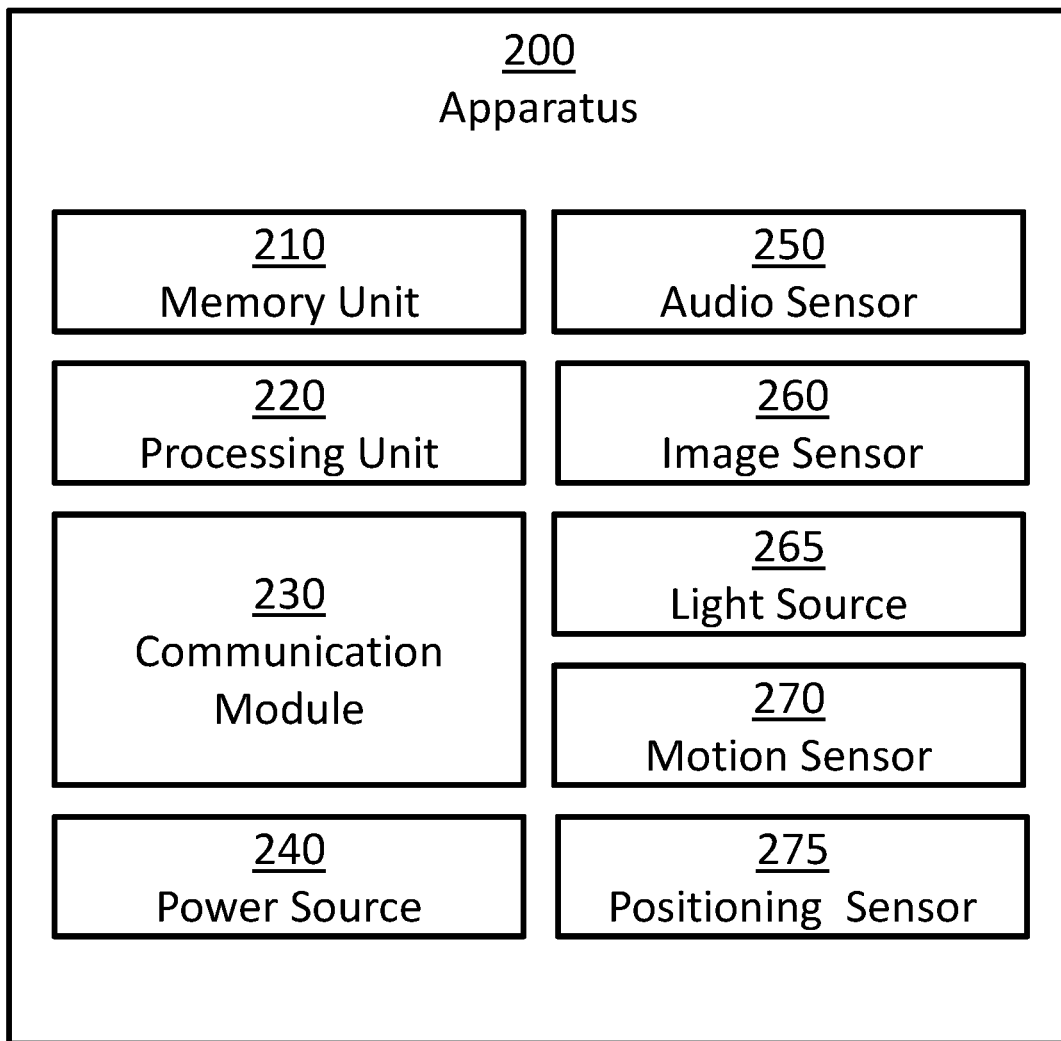

FIGS. 2B is a block diagram illustrating a possible implementation of apparatus 200. In this example, apparatus 200 may comprise: one or more memory units 210, one or more processing units 220, one or more communication modules 230, one or more power sources 240, one or more audio sensors 250, one or more image sensors 260, one or more light sources 265, one or more motion sensors 270, and one or more positioning sensors 275. In some implementations, apparatus 200 may comprise additional components, while some components listed above may be excluded. For example, in some implementations apparatus 200 may also comprise at least one of the following: one or more barometers; one or more pressure sensors; one or more proximity sensors; one or more electrical impedance sensors; one or more electrical voltage sensors; one or more electrical current sensors; one or more user input devices; one or more output devices; and so forth. In another example, in some implementations at least one of the following may be excluded from apparatus 200: memory units 210, communication modules 230, power sources 240, audio sensors 250, image sensors 260, light sources 265, motion sensors 270, and positioning sensors 275.

In some embodiments, one or more power sources 240 may be configured to: power apparatus 200; power server 300; power cloud platform 400; and/or power computational node 500. Possible implementation examples of power sources 240 may include: one or more electric batteries; one or more capacitors; one or more connections to external power sources; one or more power convertors; any combination of the above; and so forth.

In some embodiments, the one or more processing units 220 may be configured to execute software programs. For example, processing units 220 may be configured to execute software programs stored on the memory units 210. In some cases, the executed software programs may store information in memory units 210. In some cases, the executed software programs may retrieve information from the memory units 210. Possible implementation examples of the processing units 220 may include: one or more single core processors, one or more multicore processors; one or more controllers; one or more application processors; one or more system on a chip processors; one or more central processing units; one or more graphical processing units; one or more neural processing units; any combination of the above; and so forth.

In some embodiments, the one or more communication modules 230 may be configured to receive and transmit information. For example, control signals may be transmitted and/or received through communication modules 230. In another example, information received through communication modules 230 may be stored in memory units 210. In an additional example, information retrieved from memory units 210 may be transmitted using communication modules 230. In another example, input data may be transmitted and/or received using communication modules 230. Examples of such input data may include: input data inputted by a user using user input devices; information captured using one or more sensors; and so forth. Examples of such sensors may include: audio sensors 250; image sensors 260; motion sensors 270; positioning sensors 275; chemical sensors; temperature sensors; barometers; pressure sensors; proximity sensors; electrical impedance sensors; electrical voltage sensors; electrical current sensors; and so forth.

In some embodiments, the one or more audio sensors 250 may be configured to capture audio by converting sounds to digital information. Some examples of audio sensors 250 may include: microphones, unidirectional microphones, bidirectional microphones, cardioid microphones, omnidirectional microphones, onboard microphones, wired microphones, wireless microphones, any combination of the above, and so forth. In some examples, the captured audio may be stored in memory units 210. In some additional examples, the captured audio may be transmitted using communication modules 230, for example to other computerized devices, such as server 300, cloud platform 400, computational node 500, and so forth. In some examples, processing units 220 may control the above processes. For example, processing units 220 may control at least one of: capturing of the audio; storing the captured audio; transmitting of the captured audio; and so forth. In some cases, the captured audio may be processed by processing units 220. For example, the captured audio may be compressed by processing units 220; possibly followed: by storing the compressed captured audio in memory units 210; by transmitted the compressed captured audio using communication modules 230; and so forth. In another example, the captured audio may be processed using speech recognition algorithms. In another example, the captured audio may be processed using speaker recognition algorithms.

In some embodiments, the one or more image sensors 260 may be configured to capture visual information by converting light to: images; sequence of images; videos; and so forth. In some examples, the captured visual information may be stored in memory units 210. In some additional examples, the captured visual information may be transmitted using communication modules 230, for example to other computerized devices, such as server 300, cloud platform 400, computational node 500, and so forth. In some examples, processing units 220 may control the above processes. For example, processing units 220 may control at least one of: capturing of the visual information; storing the captured visual information; transmitting of the captured visual information; and so forth. In some cases, the captured visual information may be processed by processing units 220. For example, the captured visual information may be compressed by processing units 220; possibly followed: by storing the compressed captured visual information in memory units 210; by transmitted the compressed captured visual information using communication modules 230; and so forth. In another example, the captured visual information may be processed in order to: detect objects, detect events, detect action, detect face, detect people, recognize person, and so forth.

In some embodiments, the one or more light sources 265 may be configured to emit light, for example in order to enable better image capturing by image sensors 260. In some examples, the emission of light may be coordinated with the capturing operation of image sensors 260. In some examples, the emission of light may be continuous. In some examples, the emission of light may be performed at selected times. The emitted light may be visible light, infrared light, x-rays, gamma rays, and/or in any other light spectrum.

In some embodiments, the one or more motion sensors 270 may be configured to perform at least one of the following: detect motion of objects in the environment of apparatus 200; measure the velocity of objects in the environment of apparatus 200; measure the acceleration of objects in the environment of apparatus 200; detect motion of apparatus 200; measure the velocity of apparatus 200; measure the acceleration of apparatus 200; and so forth. In some implementations, the one or more motion sensors 270 may comprise one or more accelerometers configured to detect changes in proper acceleration and/or to measure proper acceleration of apparatus 200. In some implementations, the one or more motion sensors 270 may comprise one or more gyroscopes configured to detect changes in the orientation of apparatus 200 and/or to measure information related to the orientation of apparatus 200. In some implementations, motion sensors 270 may be implemented using image sensors 260, for example by analyzing images captured by image sensors 260 to perform at least one of the following tasks: track objects in the environment of apparatus 200; detect moving objects in the environment of apparatus 200; measure the velocity of objects in the environment of apparatus 200; measure the acceleration of objects in the environment of apparatus 200; measure the velocity of apparatus 200, for example by calculating the egomotion of image sensors 260; measure the acceleration of apparatus 200, for example by calculating the egomotion of image sensors 260; and so forth. In some implementations, motion sensors 270 may be implemented using image sensors 260 and light sources 265, for example by implementing a LIDAR using image sensors 260 and light sources 265. In some implementations, motion sensors 270 may be implemented using one or more RADARs. In some examples, information captured using motion sensors 270: may be stored in memory units 210, may be processed by processing units 220, may be transmitted and/or received using communication modules 230, and so forth.

In some embodiments, the one or more positioning sensors 275 may be configured to obtain positioning information of apparatus 200, to detect changes in the position of apparatus 200, and/or to measure the position of apparatus 200. In some examples, positioning sensors 275 may be implemented using one of the following technologies: Global Positioning System (GPS), GLObal NAvigation Satellite System (GLONASS), Galileo global navigation system, BeiDou navigation system, other Global Navigation Satellite Systems (GNSS), Indian Regional Navigation Satellite System (IRNSS), Local Positioning Systems (LPS), Real-Time Location Systems (RTLS), Indoor Positioning System (IPS), Wi-Fi based positioning systems, cellular triangulation, and so forth. In some examples, information captured using positioning sensors 275 may be stored in memory units 210, may be processed by processing units 220, may be transmitted and/or received using communication modules 230, and so forth.

In some embodiments, the one or more chemical sensors may be configured to perform at least one of the following: measure chemical properties in the environment of apparatus 200; measure changes in the chemical properties in the environment of apparatus 200; detect the present of chemicals in the environment of apparatus 200; measure the concentration of chemicals in the environment of apparatus 200. Examples of such chemical properties may include: pH level, toxicity, temperature, and so forth. Examples of such chemicals may include: electrolytes, particular enzymes, particular hormones, particular proteins, smoke, carbon dioxide, carbon monoxide, oxygen, ozone, hydrogen, hydrogen sulfide, and so forth. In some examples, information captured using chemical sensors may be stored in memory units 210, may be processed by processing units 220, may be transmitted and/or received using communication modules 230, and so forth.

In some embodiments, the one or more temperature sensors may be configured to detect changes in the temperature of the environment of apparatus 200 and/or to measure the temperature of the environment of apparatus 200. In some examples, information captured using temperature sensors may be stored in memory units 210, may be processed by processing units 220, may be transmitted and/or received using communication modules 230, and so forth.

In some embodiments, the one or more barometers may be configured to detect changes in the atmospheric pressure in the environment of apparatus 200 and/or to measure the atmospheric pressure in the environment of apparatus 200. In some examples, information captured using the barometers may be stored in memory units 210, may be processed by processing units 220, may be transmitted and/or received using communication modules 230, and so forth.

In some embodiments, the one or more pressure sensors may be configured to perform at least one of the following: detect pressure in the environment of apparatus 200; measure pressure in the environment of apparatus 200; detect change in the pressure in the environment of apparatus 200; measure change in pressure in the environment of apparatus 200; detect pressure at a specific point and/or region of the surface area of apparatus 200; measure pressure at a specific point and/or region of the surface area of apparatus 200; detect change in pressure at a specific point and/or area; measure change in pressure at a specific point and/or region of the surface area of apparatus 200; measure the pressure differences between two specific points and/or regions of the surface area of apparatus 200; measure changes in relative pressure between two specific points and/or regions of the surface area of apparatus 200. In some examples, information captured using the pressure sensors may be stored in memory units 210, may be processed by processing units 220, may be transmitted and/or received using communication modules 230, and so forth.

In some embodiments, the one or more proximity sensors may be configured to perform at least one of the following: detect contact of a solid object with the surface of apparatus 200; detect contact of a solid object with a specific point and/or region of the surface area of apparatus 200; detect a proximity of apparatus 200 to an object. In some implementations, proximity sensors may be implemented using image sensors 260 and light sources 265, for example by emitting light using light sources 265, such as ultraviolet light, visible light, infrared light and/or microwave light, and detecting the light reflected from nearby objects using image sensors 260 to detect the present of nearby objects. In some examples, information captured using the proximity sensors may be stored in memory units 210, may be processed by processing units 220, may be transmitted and/or received using communication modules 230, and so forth.

In some embodiments, the one or more electrical impedance sensors may be configured to perform at least one of the following: detect change over time in the connectivity and/or permittivity between two electrodes; measure changes over time in the connectivity and/or permittivity between two electrodes; capture Electrical Impedance Tomography (EIT) images. In some examples, information captured using the electrical impedance sensors may be stored in memory units 210, may be processed by processing units 220, may be transmitted and/or received using communication modules 230, and so forth.

In some embodiments, the one or more electrical voltage sensors may be configured to perform at least one of the following: detect and/or measure voltage between two electrodes; detect and/or measure changes over time in the voltage between two electrodes. In some examples, information captured using the electrical voltage sensors may be stored in memory units 210, may be processed by processing units 220, may be transmitted and/or received using communication modules 230, and so forth.

In some embodiments, the one or more electrical current sensors may be configured to perform at least one of the following: detect and/or measure electrical current flowing between two electrodes; detect and/or measure changes over time in the electrical current flowing between two electrodes. In some examples, information captured using the electrical current sensors may be stored in memory units 210, may be processed by processing units 220, may be transmitted and/or received using communication modules 230, and so forth.

In some embodiments, the one or more user input devices may be configured to allow one or more users to input information. In some examples, user input devices may comprise at least one of the following: a keyboard, a mouse, a touchpad, a touch screen, a joystick, a microphone, an image sensor, and so forth. In some examples, the user input may be in the form of at least one of: text, sounds, speech, hand gestures, body gestures, tactile information, and so forth. In some examples, the user input may be stored in memory units 210, may be processed by processing units 220, may be transmitted and/or received using communication modules 230, and so forth.

In some embodiments, the one or more user output devices may be configured to provide output information to one or more users. In some examples, such output information may comprise of at least one of: notifications, feedbacks, reports, and so forth. In some examples, user output devices may comprise at least one of: one or more audio output devices; one or more textual output devices; one or more visual output devices; one or more tactile output devices; and so forth. In some examples, the one or more audio output devices may be configured to output audio to a user, for example through: a headset, a set of speakers, and so forth. In some examples, the one or more visual output devices may be configured to output visual information to a user, for example through: a display screen, an augmented reality display system, a printer, a LED indicator, and so forth. In some examples, the one or more tactile output devices may be configured to output tactile feedbacks to a user, for example through vibrations, through motions, by applying forces, and so forth. In some examples, the output may be provided: in real time, offline, automatically, upon request, and so forth. In some examples, the output information may be read from memory units 210, may be provided by a software executed by processing units 220, may be transmitted and/or received using communication modules 230, and so forth.

In some embodiments, apparatus 200 may be included in a medical device, such as a surgical instrument, a laparoscope, thoracoscope, arthroscope, bronchoscope, endoscope, and so forth. In some embodiments, apparatus 200 may include medical monitoring devices, such as Electro-Cardio-Graphs, Electro-Encephalo-Graphs, Electro-Myo-Graphs, oximeters, and so forth. In some embodiments, apparatus 200 may be configured to be positioned in an operation room. In some embodiments, apparatus 200 may be configured to capture and/or receive information from an operation room. Some examples of such information may include videos of surgical operations, audio recordings of surgical operations, information from monitoring devices (for example, from patient data management systems, central monitoring station, tele-monitoring systems, multi-parameter monitors, patient monitors, vital signs monitor, Electro-Cardio-Graphs, Electro-Encephalo-Graphs, Electro-Myo-Graphs, oximeters, etc.), and so forth.

Figure 3:
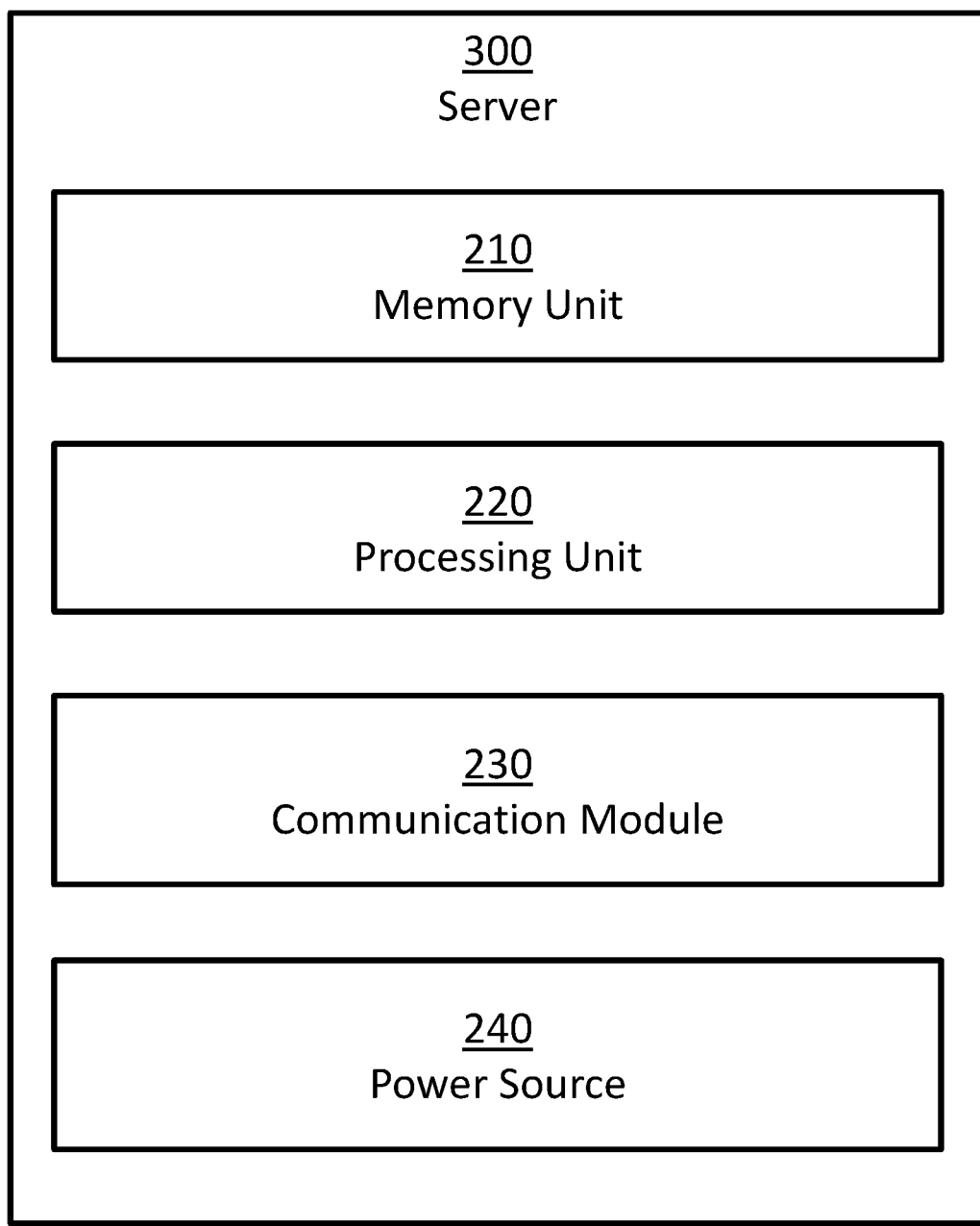
FIG. 3 is a block diagram illustrating a possible implementation of a server.

FIGS. 3 is a block diagram illustrating a possible implementation of server 300. In this example, server 300 may comprise: one or more memory units 210, one or more processing units 220, one or more communication modules 230, and one or more power sources 240. In some implementations, server 300 may comprise additional components, while some components listed above may be excluded. For example, in some implementations server 300 may also comprise at least one of the following: one or more user input devices; one or more output devices; and so forth. In another example, in some implementations at least one of the following may be excluded from server 300: memory units 210, communication modules 230, and power sources 240.

Figure 4A:
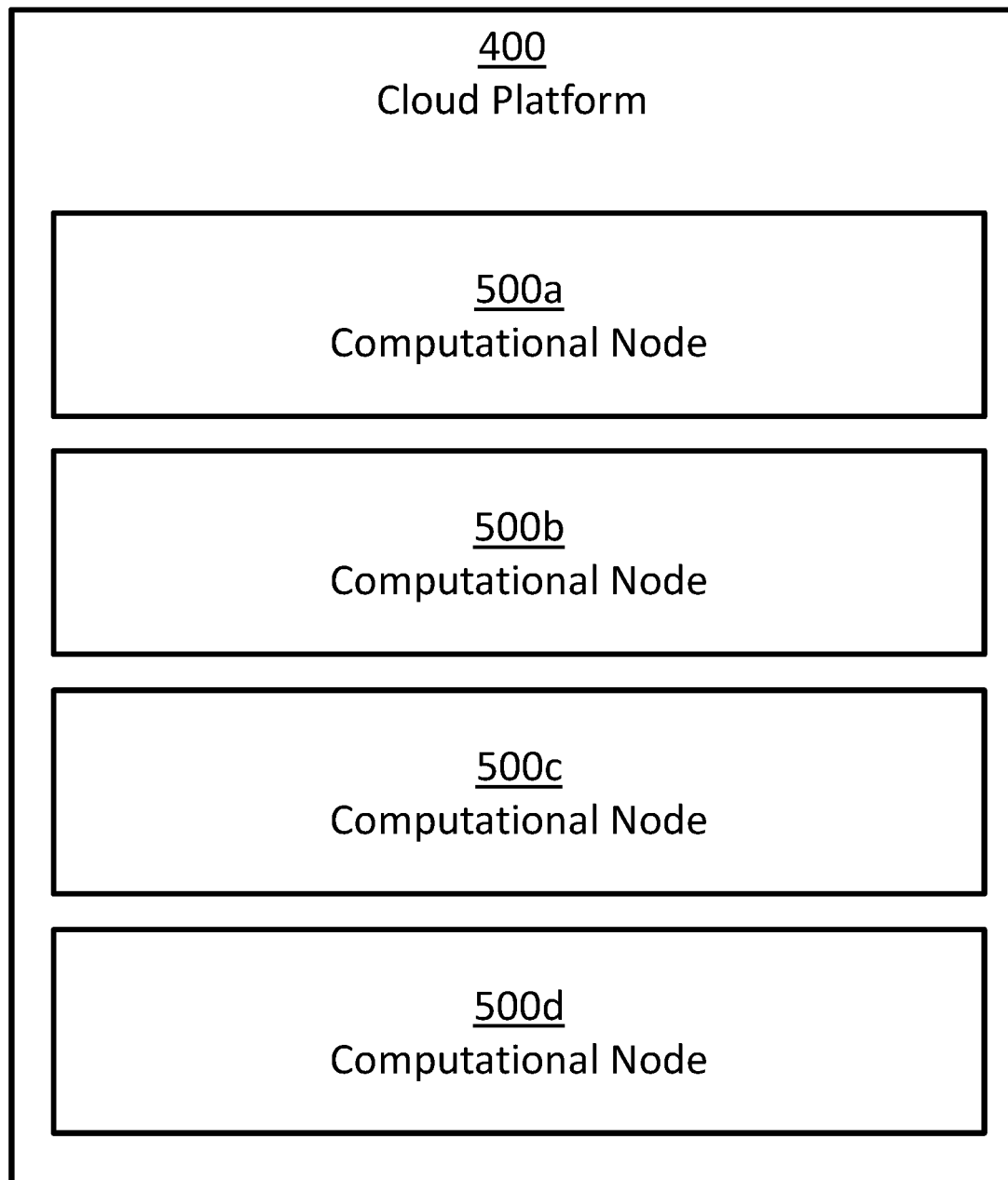
FIG. 4A and 4B are block diagrams illustrating some possible implementations of a cloud platform.

FIG. 4A is a block diagram illustrating a possible implementation of cloud platform 400. In this example, cloud platform 400 may comprise computational node 500a, computational node 500b, computational node 500c and computational node 500d. In some examples, a possible implementation of computational nodes 500a, 500b, 500c and 500d may comprise server 300 as described in FIG. 3. In some examples, a possible implementation of computational nodes 500a, 500b, 500c and 500d may comprise computational node 500 as described in FIG. 5.

Figure 4B:
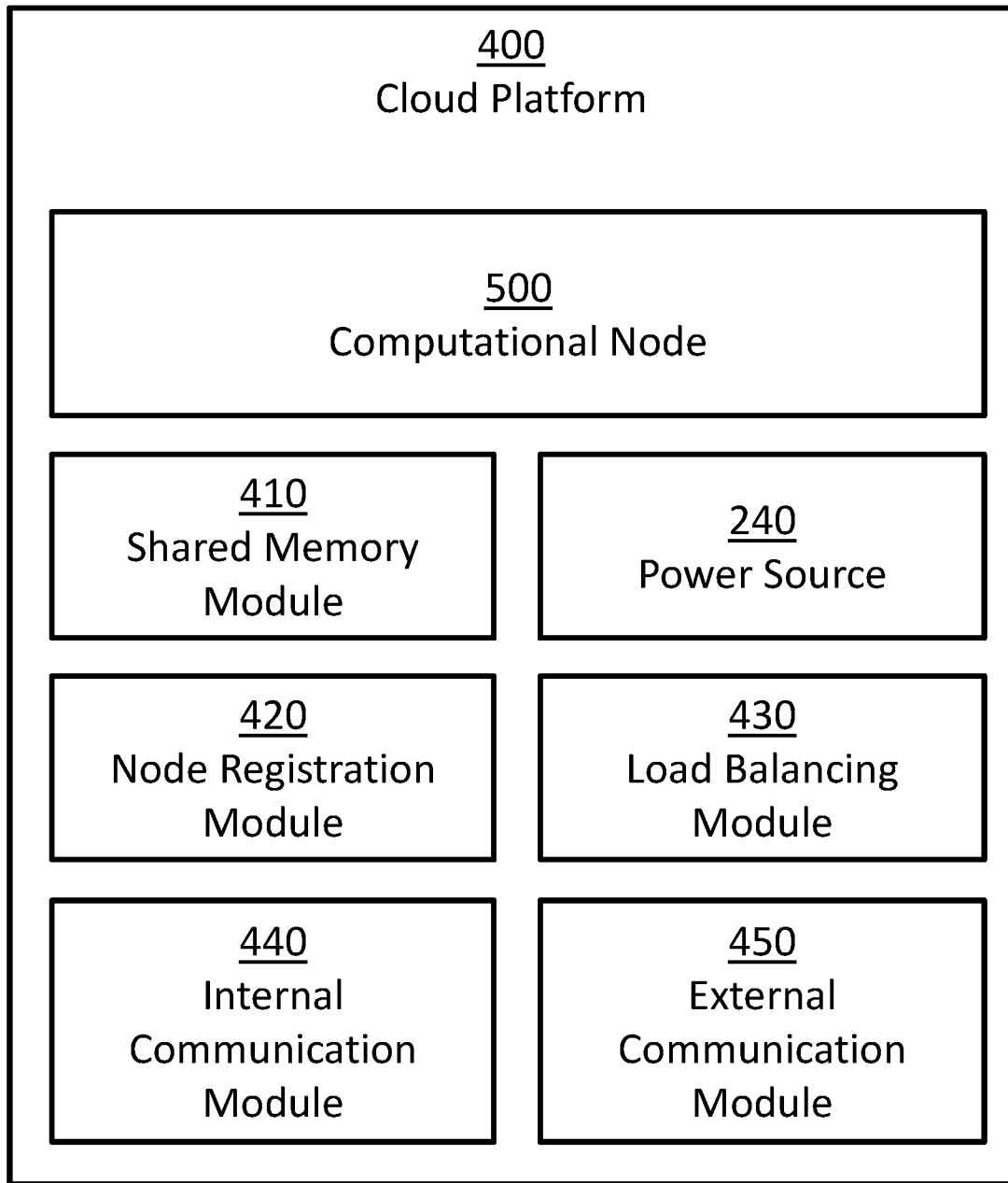

FIG. 4B is a block diagram illustrating a possible implementation of cloud platform 400. In this example, cloud platform 400 may comprise: one or more computational nodes 500, one or more shared memory modules 410, one or more power sources 240, one or more node registration modules 420, one or more load balancing modules 430, one or more internal communication modules 440, and one or more external communication modules 450. In some implementations, cloud platform 400 may comprise additional components, while some components listed above may be excluded. For example, in some implementations cloud platform 400 may also comprise at least one of the following: one or more user input devices; one or more output devices; and so forth. In another example, in some implementations at least one of the following may be excluded from cloud platform 400: shared memory modules 410, power sources 240, node registration modules 420, load balancing modules 430, internal communication modules 440, and external communication modules 450.

Figure 5:
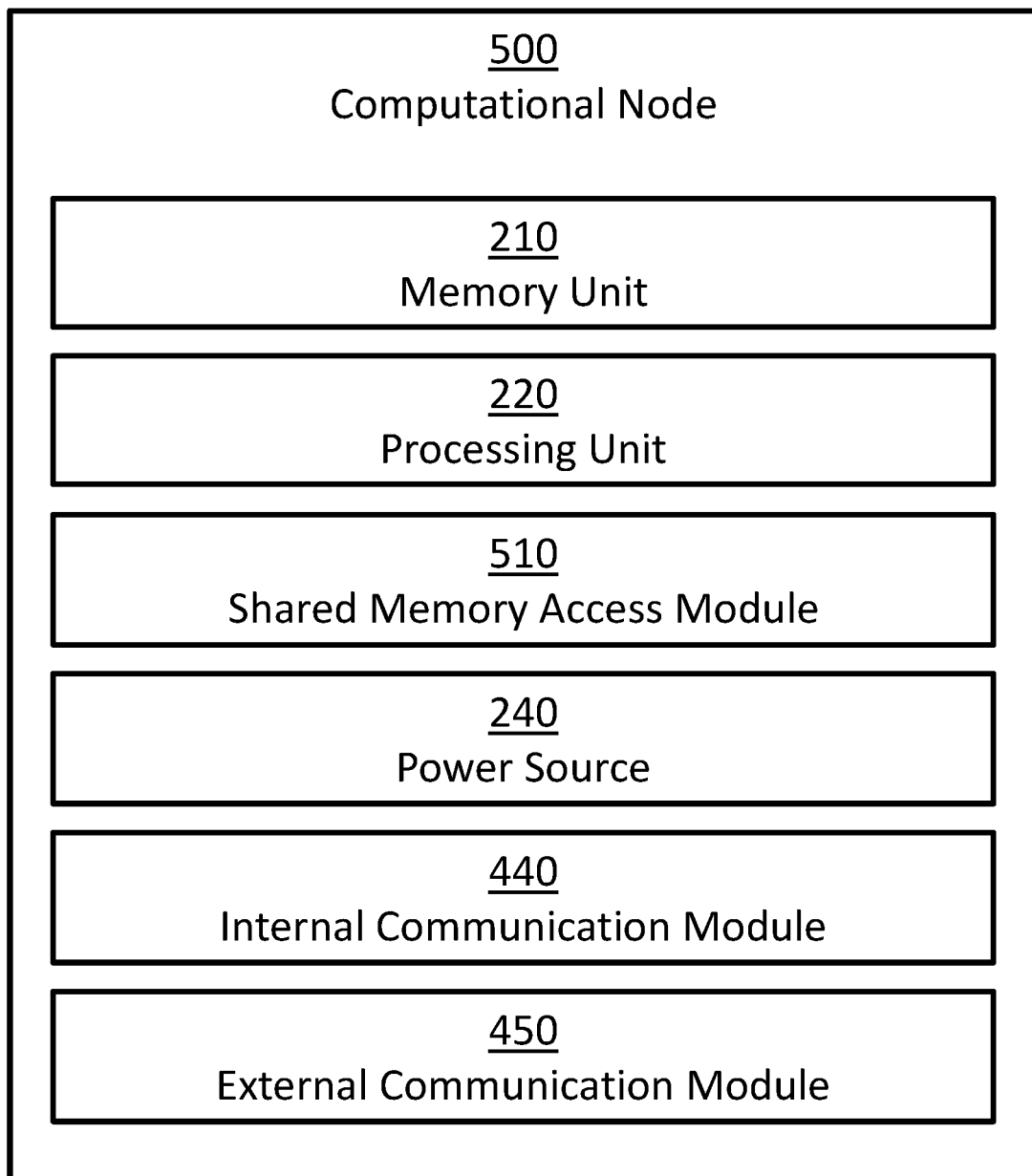
FIG. 5 is a block diagram illustrating a possible implementation of a computational node.

FIG. 5 is a block diagram illustrating a possible implementation of computational node 500. In this example, computational node 500 may comprise: one or more memory units 210, one or more processing units 220, one or more shared memory access modules 510, one or more power sources 240, one or more internal communication modules 440, and one or more external communication modules 450. In some implementations, computational node 500 may comprise additional components, while some components listed above may be excluded. For example, in some implementations computational node 500 may also comprise at least one of the following: one or more user input devices; one or more output devices; and so forth. In another example, in some implementations at least one of the following may be excluded from computational node 500: memory units 210, shared memory access modules 510, power sources 240, internal communication modules 440, and external communication modules 450.

In some embodiments, internal communication modules 440 and external communication modules 450 may be implemented as a combined communication module, such as communication modules 230. In some embodiments, one possible implementation of cloud platform 400 may comprise server 300. In some embodiments, one possible implementation of computational node 500 may comprise server 300. In some embodiments, one possible implementation of shared memory access modules 510 may comprise using internal communication modules 440 to send information to shared memory modules 410 and/or receive information from shared memory modules 410. In some embodiments, node registration modules 420 and load balancing modules 430 may be implemented as a combined module.

In some embodiments, the one or more shared memory modules 410 may be accessed by more than one computational node. Therefore, shared memory modules 410 may allow information sharing among two or more computational nodes 500. In some embodiments, the one or more shared memory access modules 510 may be configured to enable access of computational nodes 500 and/or the one or more processing units 220 of computational nodes 500 to shared memory modules 410. In some examples, computational nodes 500 and/or the one or more processing units 220 of computational nodes 500, may access shared memory modules 410, for example using shared memory access modules 510, in order to perform at least one of: executing software programs stored on shared memory modules 410, store information in shared memory modules 410, retrieve information from the shared memory modules 410.

In some embodiments, the one or more node registration modules 420 may be configured to track the availability of the computational nodes 500. In some examples, node registration modules 420 may be implemented as: a software program, such as a software program executed by one or more of the computational nodes 500; a hardware solution; a combined software and hardware solution; and so forth. In some implementations, node registration modules 420 may communicate with computational nodes 500, for example using internal communication modules 440. In some examples, computational nodes 500 may notify node registration modules 420 of their status, for example by sending messages: at computational node 500 startup; at computational node 500 shutdowns; at constant intervals; at selected times; in response to queries received from node registration modules 420; and so forth. In some examples, node registration modules 420 may query about computational nodes 500 status, for example by sending messages: at node registration module 420 startup; at constant intervals; at selected times; and so forth.

In some embodiments, the one or more load balancing modules 430 may be configured to divide the workload among computational nodes 500. In some examples, load balancing modules 430 may be implemented as: a software program, such as a software program executed by one or more of the computational nodes 500; a hardware solution; a combined software and hardware solution; and so forth. In some implementations, load balancing modules 430 may interact with node registration modules 420 in order to obtain information regarding the availability of the computational nodes 500. In some implementations, load balancing modules 430 may communicate with computational nodes 500, for example using internal communication modules 440. In some examples, computational nodes 500 may notify load balancing modules 430 of their status, for example by sending messages: at computational node 500 startup; at computational node 500 shutdowns; at constant intervals; at selected times; in response to queries received from load balancing modules 430; and so forth. In some examples, load balancing modules 430 may query about computational nodes 500 status, for example by sending messages: at load balancing module 430 startup; at constant intervals; at selected times; and so forth.

In some embodiments, the one or more internal communication modules 440 may be configured to receive information from one or more components of cloud platform 400, and/or to transmit information to one or more components of cloud platform 400. For example, control signals and/or synchronization signals may be sent and/or received through internal communication modules 440. In another example, input information for computer programs, output information of computer programs, and/or intermediate information of computer programs, may be sent and/or received through internal communication modules 440. In another example, information received through internal communication modules 440 may be stored in memory units 210, in shared memory units 410, and so forth. In an additional example, information retrieved from memory units 210 and/or shared memory units 410 may be transmitted using internal communication modules 440. In another example, input data may be transmitted and/or received using internal communication modules 440. Examples of such input data may include input data inputted by a user using user input devices.

In some embodiments, the one or more external communication modules 450 may be configured to receive and/or to transmit information. For example, control signals may be sent and/or received through external communication modules 450. In another example, information received through external communication modules 450 may be stored in memory units 210, in shared memory units 410, and so forth. In an additional example, information retrieved from memory units 210 and/or shared memory units 410 may be transmitted using external communication modules 450. In another example, input data may be transmitted and/or received using external communication modules 450. Examples of such input data may include: input data inputted by a user using user input devices; information captured from the environment of apparatus 200 using one or more sensors; and so forth. Examples of such sensors may include: audio sensors 250; image sensors 260; motion sensors 270; positioning sensors 275; chemical sensors; temperature sensors; barometers; pressure sensors; proximity sensors; electrical impedance sensors; electrical voltage sensors; electrical current sensors; and so forth.

In some embodiments, videos of surgical procedures (such as the video and/or parts of the video obtained by Step 610 as described below) may be analyzed to obtain preprocessed videos. One of ordinary skill in the art will recognize that the followings are examples, and that the videos may be preprocessed using other kinds of preprocessing methods. In some examples, a video may be preprocessed by transforming the video using a transformation function to obtain a transformed video, and the preprocessed video may comprise the transformed video. For example, the transformation function may comprise convolutions, visual filters (such as low-pass filters, high-pass filters, band-pass filters, all-pass filters, etc.), nonlinear functions, and so forth. In some examples, a video may be preprocessed by smoothing the video, for example using Gaussian convolution, using a median filter, and so forth. In some examples, a video may be preprocessed to obtain a different representation of the video. For example, the preprocessed video may comprise: a representation of at least part of the video in a frequency domain; a Discrete Fourier Transform of at least part of the video; a Discrete Wavelet Transform of at least part of the video; a time/frequency representation of at least part of the video; a representation of at least part of the video in a lower dimension; a lossy representation of at least part of the video; a lossless representation of at least part of the video; a time order series of any of the above; any combination of the above; and so forth. In some examples, a video may be preprocessed to extract edges, and the preprocessed video may comprise information based on and/or related to the extracted edges. In some examples, a video may be processed to extract visual features from the video. Some examples of such visual features may comprise information based on and/or related to: edges; corners; blobs; ridges; Scale Invariant Feature Transform (SIFT) features; temporal features; and so forth.

In some embodiments, further analysis of videos of surgical procedures may be performed on the raw videos and/or on the preprocessed videos. In some examples, the analysis of the video and/or the preprocessed video may be based, at least in part, on one or more rules, functions, procedures, neural networks, inference models, and so forth. The rules, functions, procedures, neural networks, and inference models may be applied to the raw video and/or to the preprocessed video. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, videos of surgical procedures may be analyzed to identify information related to patients and/or health professionals (such as surgeons, nurses, anesthesiologists, etc.) appearing in the videos. For example, face detectors and/or face recognition algorithms may be used to identify and/or locate the patients and/or health professionals, and information related to the identified patients and/or health professionals may be obtained (for example, from a database, from patient files, from files of the health professionals, from an Electronic Health Record (EHR) system, and so forth). Some examples of face detectors may include deep learning based face detection algorithms, appearance based face detection algorithms, color based face detection algorithms, texture based face detection algorithms, shape based face detection algorithms, motion based face detection algorithms, boosting based face detection algorithms, and so forth. Some examples of face recognition algorithms may include deep learning based face recognition algorithms, appearance based face recognition algorithms, color based face recognition algorithms, texture based face recognition algorithms, shape based face recognition algorithms, motion based face recognition algorithms, boosting based face recognition algorithms, dimensionality reduction based face recognition algorithms (such as eigenfaces, Fisherfaces, etc.), 3D face recognition algorithms, and so forth. In another example, an inference model trained using training examples to identify demographic information (such as age, gender, race, ethnicity, etc.) of a person may be used to identify demographic information of the detected patients and/or health professionals.

In some embodiments, videos of surgical procedures may be analyzed to identify information related to surgical instruments appearing in the videos. For example, object detectors may be used to identify and/or locate surgical instruments appearing in the videos, and information related to the identified surgical instruments may be obtained (for example, from a database, by measuring the surgical instruments in the video, and so forth). Some examples of object detectors may include deep learning based object detectors, appearance based object detectors, image features based object detectors, template based object detectors, and so forth.

In some embodiments, videos of surgical procedures may be analyzed to identify information related to anatomical structures appearing in the videos. For example, anatomical structure detector may be constructed by training an inference model using training examples. The training examples may comprise images depicting the anatomical structure to be detected, and in some cases images that do not depict the anatomical structure, possibly with corresponding labels. The anatomical structure detector may be used to identify and/or locate anatomical structures (such as organs, ducts, arteries, etc.) appearing in the videos In some embodiments, videos of surgical procedures may be analyzed to identify information related to intraoperative events appearing in the videos. For example, event detectors may be used to identify and/or locate intraoperative events appearing in the videos. Some examples of event detectors may include deep learning based event detectors, appearance based event detectors, image features based event detectors, motion based event detectors, template based event detectors, and so forth. In some examples, inference models (such as detectors, classification models, regression models, etc.) trained using training examples to identify properties of intraoperative events may be used to identify the properties of the detected intraoperative events. Some examples of properties of intraoperative events that may be identified may include type of the intraoperative event, health professionals related to the intraoperative event (for example, using face detectors and face recognition algorithms as described above), medical equipment related to the intraoperative event (for example, using object detectors as described above), organs related to the intraoperative event (for example, using organ detectors as described above), and so forth. For example, the intraoperative event may comprise an action of a health professional (such as insertion and/or removal and/or usage of a piece of a surgical instrument), an inference model may be trained to identify the type of the action, surgical instruments associated with the action may be identified as described above, health professionals associated with the action may be identified as described above, organs related to the action may be identified as described above, and so forth. In another example, the intraoperative event may comprise an intraoperative phase, and the inference model may be trained to identify the beginning and the ending of the phase, the type of the phase, and so forth. In yet another example, the intraoperative event may comprise an intraoperative adverse event and/or intraoperative complication and/or an intraoperative error, and an inference model may be trained to identify severity grade, resulting change to the operative approach, causes, required intervention, expected consequences to the patient, and so forth. In another example, the intraoperative event may comprise a bleeding, and an inference model may be trained to identify an amount of bleeding, a rate of bleeding, source of bleeding, and so forth. In yet another example, the intraoperative event may comprise a leak, and an inference model may be trained to identify leaked amount, leak rate, source of leak, type of content leaked, and so forth. In another example, the intraoperative event may comprise an injury, and an inference model may be trained to identify type of injury, location of injury, and so forth. In some examples, a region of the video depicting the intraoperative event may be identified using the event detector. For example, the region may be contained in one or more frames, and time index corresponding to at least one frame (such as the earliest frame, the last frame, the middle frame, etc.) may be associated with the intraoperative event. In another example, the region may comprise a segment of at least one frame.

In some embodiments, process 600 may comprise of one or more steps. In some examples, process 600, as well as all individual steps therein, may be performed by various aspects of apparatus 200, server 300, cloud platform 400, computational node 500, and so forth. For example, the process may be performed by processing units 220 executing software instructions stored within memory units 210 and/or within shared memory modules 410. In some examples, process 600, as well as all individual steps therein, may be performed by a dedicated hardware. In some examples, computer readable medium (such as a non-transitory computer readable medium) may store data and/or computer implementable instructions for carrying out process 600. Some examples of possible execution manners of process 600 may include continuous execution (for example, returning to the beginning of the process once the process normal execution ends), periodically execution, executing the process at selected times, execution upon the detection of a trigger (some examples of such trigger may include a trigger from a user, a trigger from another process, a trigger from an external device, etc.), and so forth.

Figure 6:
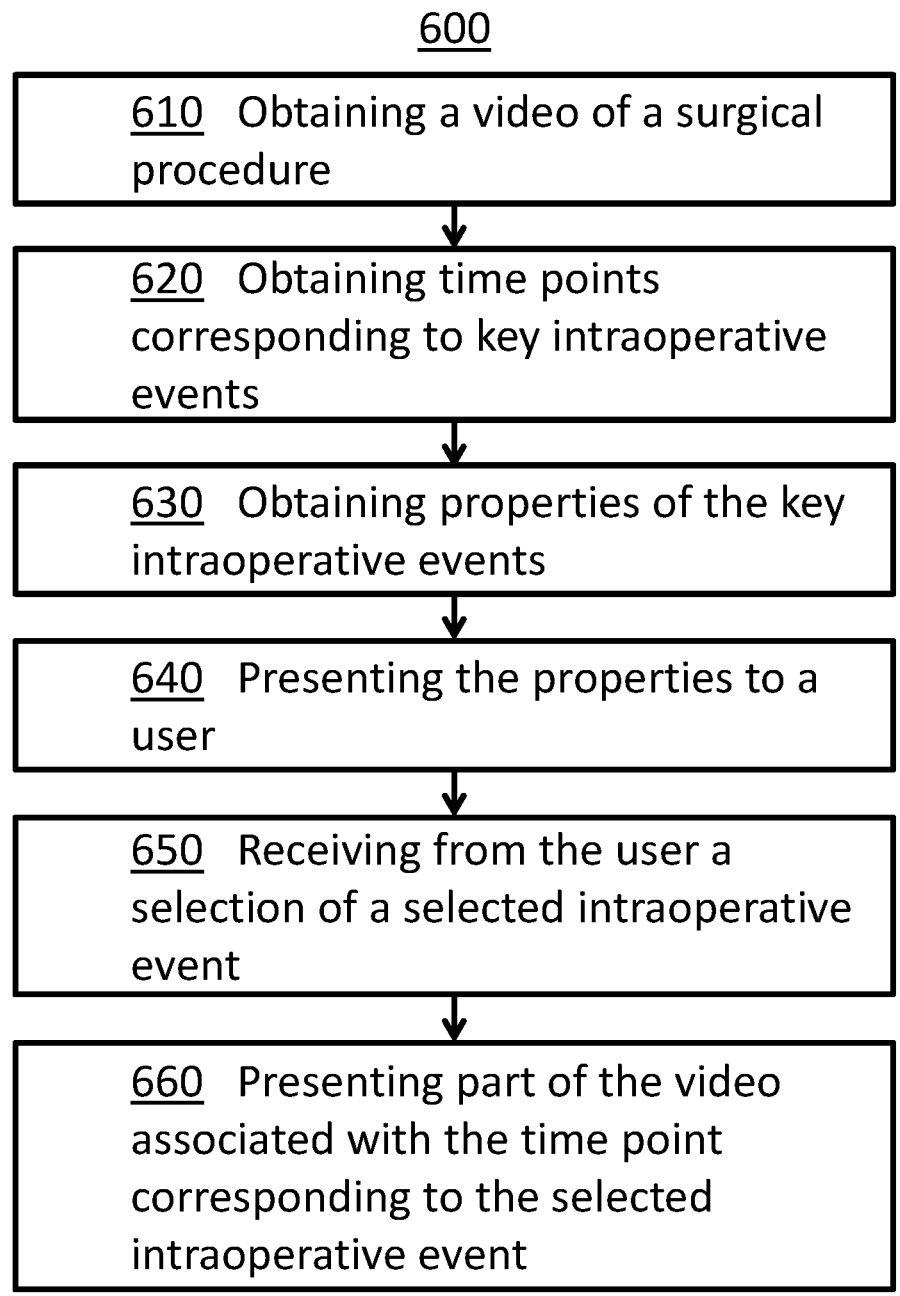
FIG. 6 illustrates an example of a process for presentation of videos of surgical procedures.

FIG. 6 illustrates an example of a process 600 for presentation of videos of surgical procedures. In this example, process 600 may comprise: obtaining a video of a surgical procedure (Step 610); obtaining time points corresponding to key intraoperative events (Step 620); obtaining properties of the key intraoperative events (Step 630); presenting the properties to a user (Step 640); receiving from the user a selection of a selected intraoperative event (Step 650); and presenting part of the video associated with the time point corresponding to the selected intraoperative event (Step 660). In some implementations, process 600 may comprise one or more additional steps, while some of the steps listed above may be modified or excluded. For example, in some cases Step 610 and/or Step 620 and/or Step 630 and/or Step 640 and/or Step 650 and/or Step 660 may be excluded from process 600. In some implementations, one or more steps illustrated in FIG. 6 may be executed in a different order and/or one or more groups of steps may be executed simultaneously and vice versa.

In some embodiments, Step 610 may comprise obtaining a video of a surgical procedure (Step 610). In some examples, at least part of the video may be read from memory (such as memory units 210, shared memory modules 410, and so forth). In some examples, at least part of the video may be received from external devices, for example using communication devices, such as communication modules 230, internal communication modules 440, external communication modules 450, and so forth. In some examples, at least part of the video may be captured, for example using image sensors 260 and/or audio sensors 250. For example, the video may be captured and provided to the process in real time. In another example, the video may be captured and provided to the process offline, for example after the recording of the video is completed. In some examples, the video may depict one or more surgical procedures. Some examples of such surgical procedures may include a laparoscopic surgery, a thoracoscopic procedure, a bronchoscopic procedure, a microscopic procedure, an open surgery, a robotic surgery, an appendectomy, a carotid endarterectomy, a carpal tunnel release, a cataract surgery, a cesarean section, a cholecystectomy, a colectomy (such as a partial colectomy, a total colectomy, etc.), a coronary angioplasty, a coronary artery bypass, a debridement (for example of a wound, a burn, an infection, etc.), a free skin graft, a hemorrhoidectomy, a hip replacement, a hysterectomy, a hysteroscopy, an inguinal hernia repair, a knee arthroscopy, a knee replacement, a mastectomy (such as a partial mastectomy, a total mastectomy, a modified radical mastectomy, etc.), a prostate resection, a prostate removal, a shoulder arthroscopy, a spine surgery (such as a spinal fusion, a laminectomy, a foraminotomy, a diskectomy, a disk replacement, an interlaminar implant, etc.), a tonsillectomy, a cochlear implant procedure, brain tumor (for example meningioma, etc.) resection, interventional procedures such as percutaneous transluminal coronary angioplasty, transcatheter aortic valve replacement, minimally Invasive surgery for intracerebral hemorrhage evacuation, and so forth.

In some embodiments, the video obtained by Step 610 may be selected of a plurality of alternative videos of surgical procedures. For example, the plurality of alternative videos of surgical procedures may be stored in memory (such as memory units 210, shared memory modules 410, and so forth), in a video server (such as server 300), in a cloud (such as cloud platform 400), and so forth. In some examples, the video may be selected by a user. For example, a list of available videos of surgical procedures may be presented to the user, and the user may select the video from the list. For example, the list of available videos of surgical procedures may be presented unsorted, sorted according to the types of surgical procedures depicted in the videos, sorted according to intraoperative events depicted in the videos, sorted according to intraoperative complications depicted in the videos, sorted according to patients associated with the videos (for example, according to patients depicted in the videos of surgical procedures, according to demographic information associated with the patients, etc.), sorted according to health professionals associated with the videos (for example, according to health professionals involved in a surgical procedures depicted in the videos, according to types of the health professionals, according to the experience of the health professionals, etc.), sorted according to health centers associated with the videos (for example, according to health centers from which the videos of surgical procedures originated, according to the types of the health centers, according to the sizes of the health centers, according to geographical locations of the health centers, etc.), sorted according to any combination of the above, and so forth. In some cases, the list of available videos of surgical procedures presented to the user may be selected of the plurality of alternative videos of surgical procedures by an automatic process, for example as described below.

In some embodiments, the video obtained by Step 610 (and/or the list of available videos of surgical procedures presented to the user) may be selected of a plurality of alternative videos of surgical procedures using some additional information. In some examples, the additional information used to select the video (and/or the list of available videos of surgical procedures) may comprise information related to one or more patients. For example, the information related to the patients may be obtained from a user, from patient files, from an Electronic Health Record (EHR) system, and so forth. For example, the information related to the patients may comprise medical records and/or medical history and/or medical conditions of the patients, and videos associated with patients with similar medical records and/or medical history and/or medical conditions may be selected. In some cases, the medical history may comprise surgical history (such a list of surgeries performed on the patient, operative reports, etc.), obstetric history (such as a list of pregnancies, possibly together with details associated with the pregnancies, such as complications, outcomes, etc.), allergies, past and present medications, immunization history, growth chart and/or development history, notes from past medical encounters (for example, such note may include details about the complaints, physical examinations, medical assessment, diagnosis, etc.), test results, medical images (such as X-ray images, Computed Tomography images, Magnetic Resonance Imaging images, Positron Emission Tomography images, Single-Photon Emission Computed Tomography images, UltraSound images, Electro-Cardio-Graphy images, Electro-Encephalo-Graphy images, Electro-Myo-Graphy images, Magneto-Encephalo-Graphy images, etc.) and/or information based on medical images, medical videos and/or information based on medical videos, orders, prescriptions, medical history of the patient's family, and so forth. In another example, the information related to the patients may comprise demographic information (such as age, gender, race, ethnicity, education, profession, occupation, income level, marital status, etc.), and videos associated with patients with similar demographic information may be selected. In yet another example, a similarity function that measures the similarity between two patients may be used to measure the similarities of a selected patient to patients associated with the plurality of alternative videos of surgical procedures, and videos corresponding to high similarities may be selected (for example, the video corresponding to the highest similarity may be selected, a selected number of videos corresponding to the highest similarities may be selected, all videos corresponding to similarities higher than a selected threshold may be selected, and so forth).

In some examples, the additional information used to select the video (and/or the list of available videos of surgical procedures) may comprise information related to one or more health professionals, such as surgeons, nurses, anesthesiologists, and so forth. For example, the information related to health professionals may be obtained from a user, from files of the health professionals, from an Electronic Health Record (EHR) system, and so forth. For example, the information related to the health professionals may comprise information related to past experience of the health professionals, and videos associated with health professionals with similar past experience may be selected. Some examples of information related to past experience of the health professionals may include information related to the type and/or level of training of the health professionals, surgeries that the health professionals were involved in, number of surgeries performed by the health professionals, types of surgeries performed by the health professionals, number of surgeries of selected types performed by the health professionals, past surgical outcomes, past surgical complications, and so forth. In another example, the information related to the health professionals may comprise demographic information, and videos associated with health professionals with similar demographic information may be selected. In yet another example, a similarity function that measures the similarity between two health professionals may be used to measure the similarities of a selected health professional to health professionals associated with the plurality of alternative videos of surgical procedures, and videos corresponding to high similarities may be selected. In another example, a similarity function that measures the similarity between two groups of health professionals may be used to measure the similarities of a selected group of two or more health professionals to groups of health professionals associated with the plurality of alternative videos of surgical procedures, and videos corresponding to high similarities may be selected. For example, the video corresponding to the highest similarity may be selected, a selected number of videos corresponding to the highest similarities may be selected, all videos corresponding to similarities higher than a selected threshold may be selected, and so forth.

In some examples, the additional information used to select the video (and/or the list of available videos of surgical procedures) may comprise information related to one or more planned surgical procedures. For example, the information related to planned surgical procedures may be obtained from a user, from patients' files, from surgeons' notes, from an Electronic Health Record (EHR) system, and so forth. For example, videos of surgical procedures associated with similar information may be selected. Some examples of information related to the planned surgical procedures may comprise information related to patients involved in the planned surgical procedures (for example, as described above), to health professionals involved in the planned surgical procedures (for example, as described above), to the types of the planned surgical procedures, to the types of anesthesia of the planned surgical procedures, to health centers associated with the planned surgical procedures, to surgical techniques associated with the planned surgical procedures, to pieces of equipment (such as surgical instruments) associated with the planned surgical procedures, to information related to surgical planning of the planned surgical procedures, and so forth. For example, a similarity function that measures the similarity between two surgical procedures may be used to measure the similarities of the planned surgical procedures to the surgical procedures associated with the plurality of alternative videos of surgical procedures, and videos corresponding to high similarities may be selected (for example, the video corresponding to the highest similarity may be selected, a selected number of videos corresponding to the highest similarities may be selected, all videos corresponding to similarities higher than a selected threshold may be selected, and so forth).

In some examples, the additional information used to select the video (and/or the list of available videos of surgical procedures) may comprise information related to one or more possible outcomes of surgical procedures (such as successful outcomes, failures to cure, complications, sequelae, and so forth). For example, the information related to possible outcomes of surgical procedures may be obtained from a user, from a database that associates surgical procedures with some possible outcomes (such as complications, sequelae, etc.), from an inference model that predicts the likely outcomes of planned surgical procedures (for example, using the information related to planned surgical procedures described above), and so forth. For example, videos of surgical procedures associated with similar outcomes may be selected. Some examples of information related to possible failures to cure may comprise causes of failure, degree of failure, indications of failures, level of patient satisfaction, need for reoperation, and so forth. Some examples of information related to possible complications may comprise type, severity grade, required intervention (for example, with medications, with invasive procedures, with blood transfusions, with parenteral nutrition, etc.), length of hospital stay (for example, beyond normal hospital stay for the surgical procedure), lasting disabilities, organ dysfunction, organ resections, death due to the complication, cost of care, and so forth. Some examples of information related to possible sequelae may comprise type of sequelae, severity of sequelae, and so forth. In another example, a similarity function that measures the similarity between two outcomes of surgical procedures may be used to measure the similarities of a selected outcome of surgical procedures to outcomes associated with the plurality of alternative videos of surgical procedures, and videos corresponding to high similarities may be selected. In yet another example, a similarity function that measures the similarity between two groups of outcomes of surgical procedures (for example, two groups of complications) may be used to measure the similarities of a selected group of two or more outcomes of surgical procedures to groups of outcomes of surgical procedures associated with the plurality of alternative videos of surgical procedures, and videos corresponding to high similarities may be selected. For example, the video corresponding to the highest similarity may be selected, a selected number of videos corresponding to the highest similarities may be selected, all videos corresponding to similarities higher than a selected threshold may be selected, and so forth.

In some examples, the additional information used to select the video (and/or the list of available videos of surgical procedures) may comprise information related to one or more possible intraoperative events. Some examples of intraoperative events may include intraoperative adverse events, intraoperative complications, intraoperative errors, actions (for example, of a health professional), usage of surgical instruments, and so forth. Some examples of intraoperative adverse events may include bleeding, mesenteric emphysema, injury, conversion to unplanned open surgery (for example, abdominal wall incision), incision significantly larger than planned, and so forth. Some examples of intraoperative complications may include hypertension, hypotension, bradycardia, hypoxemia, adhesions, hernias, atypical anatomy, and so forth. Some examples of intraoperative errors may include technical errors, communication errors, management errors, judgment errors, decision making errors, errors related to medical equipment utilization, dural tears, perforator injury, arterial occlusions, miscommunication, and so forth. For example, the information related to possible intraoperative events may be obtained from a user, from a database that associates surgical procedures with some possible intraoperative events, from an inference model that predicts the likely intraoperative events of planned surgical procedures (for example, using the information related to planned surgical procedures described above), and so forth. For example, videos of surgical procedures associated with similar intraoperative events may be selected. Some examples of information related to possible intraoperative adverse events may comprise type, time, causes, related organs, severity grade, required intervention, resulting change to the operative approach, expected consequences to the patient, and so forth. Some examples of information related to possible intraoperative complications may comprise type, time, related organs, severity grade, resulting change to the operative approach, and so forth. Some examples of information related to possible intraoperative errors may comprise type, time, severity grade, related health professionals, related organs, related equipment, results, and so forth. In another example, a similarity function that measures the similarity between two intraoperative events may be used to measure the similarities of a selected intraoperative event to intraoperative events associated with the plurality of alternative videos of surgical procedures, and videos corresponding to high similarities may be selected. In yet another example, a similarity function that measures the similarity between two groups of intraoperative events may be used to measure the similarities of a selected group of two or more intraoperative events to groups of intraoperative events associated with the plurality of alternative videos of surgical procedures, and videos corresponding to high similarities may be selected. For example, the intraoperative events associated with the plurality of alternative videos of surgical procedures may be obtained from incident reports, surgical debriefing, a database, analysis of the videos of surgical procedures (for example, as described above), and so forth. For example, the video corresponding to the highest similarity may be selected, a selected number of videos corresponding to the highest similarities may be selected, all videos corresponding to similarities higher than a selected threshold may be selected, and so forth.

In some examples, the additional information used to select the video (and/or the list of available videos of surgical procedures) may comprise information related to one or more surgical instruments. For example, the information related to surgical instruments may be obtained from a user, from operative records, from incident reports, from surgical debriefings, from an Electronic Health Record (EHR) system, from a database that associates surgical procedures with surgical instruments, from an inference model that predicts the likely surgical instruments to be used in planned surgical procedures (for example, using the information related to planned surgical procedures described above), and so forth. Some examples of surgical instruments may include cutting instruments (such as scalpels, scissors, saws, etc.), grasping and/or holding instruments (such as Billroth's clamps, hemostatic "mosquito" forceps, atraumatic hemostatic forceps, Deschamp's needle, Höpfner's hemostatic forceps, etc.), retractors (such as Farabef's C-shaped laminar hook, blunt-toothed hook, sharp-toothed hook, grooved probe, tamp forceps, etc.), tissue unifying instruments and/or materials (such as needle holders, surgical needles, staplers, clips, adhesive tapes, mesh, etc.), protective equipment (such as facial and/or respiratory protective equipment, headwear, footwear, gloves, etc.), laparoscopes, endoscopes, patient monitoring devices, and so forth. For example, videos of surgical procedures associated with similar surgical instruments and/or with surgical instruments related to similar information may be selected. Some examples of information related to surgical instruments may comprise types, models, manufacturers, measurements, materials composing the surgical instruments, and so forth. In another example, a similarity function that measures the similarity between two surgical instruments may be used to measure the similarities of a selected surgical instrument to surgical instruments associated with the plurality of alternative videos of surgical procedures, and videos corresponding to high similarities may be selected. In another example, a similarity function that measures the similarity between two groups of surgical instruments may be used to measure the similarities of a selected group of two or more surgical instruments to groups of surgical instruments associated with the plurality of alternative videos of surgical procedures, and videos corresponding to high similarities may be selected. For example, the video corresponding to the highest similarity may be selected, a selected number of videos corresponding to the highest similarities may be selected, all videos corresponding to similarities higher than a selected threshold may be selected, and so forth.

In some examples, the additional information used to select the video (and/or the list of available videos of surgical procedures) may comprise a second group of one or more videos and/or information related to a second group of one or more videos. For example, the second group of videos may comprise videos obtained using Step 610 and/or presented using Step 660, for example by another instance of process 600. For example, videos of surgical procedures similar to the videos of the second group and/or associated with similar information to the information related to the second group may be selected. Some examples of information related to the second group of videos may comprise information obtained by analyzing the videos (for example, as described above), information related to the surgical procedures depicted in the videos, information related to patients involved in surgical procedures depicted in the videos (for example, as described above), information related to health professionals involved in surgical procedures depicted in the videos (for example, as described above), information related to pieces of equipment used in surgical procedures depicted in the videos (for example, as described above), information related to intraoperative events of surgical procedures depicted in the videos (for example, as described above), and so forth. For example, a similarity function that measures the similarity between two videos and/or between two groups of videos and/or between information related to two videos and/or between information related to two groups of videos may be used to measure the similarities of the second group of videos and/or information related to the second group of videos to the plurality of alternative videos of surgical procedures and/or information related to the plurality of alternative videos, and videos of the plurality of alternative videos corresponding to high similarities may be selected (for example, the video corresponding to the highest similarity may be selected, a selected number of videos corresponding to the highest similarities may be selected, all videos corresponding to similarities higher than a selected threshold may be selected, and so forth).

In some embodiments, obtaining time points corresponding to key intraoperative events (Step 620) may comprise obtaining a plurality of time points corresponding to a plurality of key intraoperative events in videos of surgical procedures (for example, in the video of a surgical procedure obtained by Step 610). Some examples of key intraoperative events may include intraoperative phases, intraoperative adverse events, intraoperative complications, intraoperative errors, actions (for example, of a health professional), and so forth. Some examples of such actions may include insertion and/or removal and/or usage of a piece of medical equipment (such as a surgical instrument). Some examples of intraoperative adverse events may include bleeding, mesenteric emphysema, injury, conversion to unplanned abdominal wall incision, incision significantly larger than planned, and so forth. Some examples of intraoperative complications may include hypertension, hypotension, bradycardia, hypoxemia, adhesions, hernias, atypical anatomy, and so forth. Some examples of intraoperative errors may include technical errors, communication errors, management errors, judgment errors, errors related to medical equipment, dural tears, perforator injury, arterial occlusions, miscommunication, and so forth. For example, some examples of intraoperative phases of a laparoscopic cholecystectomy surgery may include trocar placement, preparation, calot's triangle dissection, clipping and cutting of cystic duct and artery, gallbladder dissection, gallbladder packaging, cleaning and coagulation of liver bed, gallbladder retraction, and so forth. In another example, some examples of intraoperative phases of a cataract surgery may include preparation, povidone-iodine injection, corneal incision, capsulorhexis, phacoemulsification, cortical aspiration, intraocular-lens implantation, intraocular-lens adjustment, wound sealing, and so forth. In yet another example, some examples of intraoperative phases of a pituitary surgery may include preparation, nasal incision, nose retractor installation, access to the tumor, tumor removal, column of nose replacement, suturing, nose compress installation, and so forth. Some other examples of intraoperative phases may include preparation, incision, laparoscope positioning, suturing, and so forth.

In some examples, at least part of the time points may be read from memory (such as memory units 210, shared memory modules 410, and so forth). In some examples, at least part of the time points may be received from external devices, for example using communication devices, such as communication modules 230, internal communication modules 440, external communication modules 450, and so forth. In some examples, at least part of the time points and/or the key intraoperative events in the videos may be identified by analyzing the videos, for example as described above. In some examples, at least part of the time points may be obtained from operative records, incident reports, surgical debriefings, an Electronic Health Record (EHR) system, and so forth. For example, such records may comprise a textual listing of some intraoperative events, for example together with corresponding time indices, description of the intraoperative events, etc., and the textual listing may be analyzed, for example using a natural language processing algorithm, to identify the intraoperative events, the corresponding time indices, the properties of the events, and so forth. Of the identified intraoperative events, the key intraoperative events may be selected, for example using a heuristic rule, using an inference model trained using training examples to select key intraoperative events of a list of intraoperative events, and so forth.

In some embodiments, a plurality of alternative intraoperative events in the video of a surgical procedure obtained by Step 610 may be obtained, for example by analyzing the video as described above. In some examples, the sequence of the intraoperative events in time may be analyzed to identify the key intraoperative events of Step 620. In some examples, a sequence of intraoperative events of a first type may be compared with a sequence of intraoperative events of a second type to determine whether an event of a first type is a key intraoperative event. For example, a time window may be selected, and the sequences may comprise intraoperative events from the time window. In another example, the sequences may be analyzed using a Viterbi model, the parameters of the Viterbi model corresponding to the first type may be compared with the parameters of the Viterbi model corresponding to the second type, the difference between parameters of the two models may be calculated and compared with a selected threshold, and based on the result of the comparison, an event of the first type may be identified as a key intraoperative event. In some examples, the distribution of intraoperative events of a first type may be compared with a distribution of intraoperative events of a second type, for example in a time window, to determine whether an event of a first type is a key intraoperative event. For example, a statistical distance (such as f-divergence, Kullback-Leibler divergence, Hellinger distance, Total variation distance, Rényi's divergence, Jensen-Shannon divergence, Lévy-Prokhorov metric, Bhattacharyya distance, Kantorovich metric, Tsallis divergence, etc.) between the two distributions may be computed, the statistical distance may be compared with a selected threshold, and based on the result of the comparison, an event of the first type may be identified as a key intraoperative event.

In some embodiments, Step 630 may comprise obtaining properties of intraoperative events, such as properties of the key intraoperative events obtained by Step 620. In some examples, at least part of the properties may be read from memory (such as memory units 210, shared memory modules 410, and so forth). In some examples, at least part of the properties may be received from external devices, for example using communication devices, such as communication modules 230, internal communication modules 440, external communication modules 450, and so forth. In some examples, at least part of the properties may be identified by analyzing videos of the surgical procedures (such as the video obtained by Step 610), for example as described above. In some examples, at least part of the properties may be obtained from operative records, incident reports, surgical debriefing, from an Electronic Health Record (EHR) system, and so forth. For example, textual information included in such records may be analyzed, for example using a natural language processing algorithm, to identify the properties of the intraoperative events.

Some examples of properties of the intraoperative events may include type of the event, time of the event, health professionals related to the event, medical equipment related to the event, anatomical structures and/or organs related to the event, and so forth. For example, the intraoperative event may include an intraoperative phase, and some additional examples of properties of the intraoperative event may include length of the intraoperative phase, intraoperative errors and/or intraoperative adverse events and/or intraoperative complications that occurred in the intraoperative phase, actions performed in the intraoperative phase, and so forth. In another example, the intraoperative event may include an intraoperative adverse event and/or intraoperative complications and/or intraoperative error, and some additional examples of properties of the intraoperative event may include severity grade, resulting change to the operative approach, causes, required intervention, expected consequences to the patient, and so forth. In yet another example, the intraoperative event may include a bleeding, and some additional examples of properties of the intraoperative event may include an amount of bleeding, a rate of bleeding, source of bleeding, and so forth. In another example, the intraoperative event may include a leak, and some additional examples of properties of the intraoperative event may include leaked amount, leak rate, source of leak, type of content leaked, and so forth. In another example, the intraoperative event may include an injury, and some additional examples of properties of the intraoperative event may include type of injury, location of injury, and so forth.

In some embodiments, presenting the properties to a user (Step 640) may comprise presenting the properties obtained by Step 630 of the plurality of key intraoperative events of Step 620 to a user. In some examples, the properties may be presented to a user visually, for example using a graphical user interface, using a web site, using a display system, using an augmented reality system, using a virtual reality system, in a printed form, and so forth. In some examples, the properties may be presented audibly, for example through audio speakers, using headset, and so forth. For example, the properties may be presented in a list, and an entry of the list may correspond to an intraoperative event and comprise information describing the intraoperative event.

In some embodiments, receiving from the user a selection of a selected intraoperative event (Step 650) may comprise receiving from a user a selection of a selected intraoperative event of the intraoperative events of Step 620, for example in response to the presentation of properties of the intraoperative events by Step 640.

In some embodiments, presenting part of the video associated with the time point corresponding to the selected intraoperative event (Step 660) may comprise visually presenting part of the video obtained by Step 610 that is associated with the time point of the time points of Step 620 that corresponds to the selected intraoperative event received by Step 650, for example in response to the selection received by Step 650. In some examples, the part of the video may be visually presented to a user using a graphical user interface, using a web site, using a display system, using an augmented reality system, using a virtual reality system, in a printed form, using an external device, and so forth. In some examples, the presented part of the video may comprise a portion of a single frame depicting the selected intraoperative event, a single frame depicting the selected intraoperative event, a portion of a sequence of frames depicting the selected intraoperative event, a video clip depicting the selected intraoperative event, and some forth. In some examples, the video may be played starting from the frame corresponding to the time point.

In some examples, properties of the selected intraoperative event (for example, the properties obtained by Step 620) may be presented in conjunction with the part of the video presented by Step 660. In some examples, the properties may be presented next to the presented part of the video, as an overlay over the presented part of the video, as an overlay over and/or next to a region associated with the intraoperative event (for example, a region associated with the intraoperative event identified as described above), and so forth. For example, the presented information may comprise a type of the event, time or timer of time within the surgery, time and/or timer of time within the intraoperative event, information of health professionals associated with the event, information of medical equipment associated with the event, information of anatomical structures and/or organs related to the event, and so forth. For example, the selected intraoperative event may include an intraoperative phase, and the presented information may further comprise length of the intraoperative phase, information about intraoperative errors and/or intraoperative adverse events and/or intraoperative complications that occurred in the intraoperative phase, information about actions performed in the intraoperative phase, and so forth. In another example, the selected intraoperative event may include intraoperative adverse event and/or intraoperative complication and/or intraoperative error, and the presented information may further comprise severity grade, resulting change to the operative approach, causes, required intervention, expected consequences to the patient, and so forth. In yet another example, the selected intraoperative event may include a bleeding, and the presented information may further comprise an amount of bleeding, a rate of bleeding, a source of bleeding, and so forth. In another example, the selected intraoperative event may include a leak, and the presented information may further comprise leaked amount, leak rate, source of leak, type of content leaked, and so forth. In yet another example, the selected intraoperative event may include an injury, and the presented information may further comprise type of injury, location of injury, and so forth.

In some examples, recommended additional videos of surgical procedures may be selected (for example, as described above for Step 610) using the selected intraoperative event received by Step 650, the properties of the selected intraoperative event obtained by Step 630, the part of the video presented by Step 660, information related to the presented part of the video, information presented in conjunction to the presented part of the video, and so forth. Further, the recommended additional videos of surgical procedures may be presented in conjunction with the presentation of the part of the video by Step 660. In response, a user may select one of the recommended additional videos, and process 600 may repeat with the selected video, new instance of process 600 may be launched with the selected new video, and so forth. For example, the selection of the video may be performed by Step 610, and process 600 may continue with the newly selected video from Step 610.

What is claimed is:

1. A method for presentation of videos of surgical procedures, the method comprising:
    obtaining information related to a planned surgical procedure, the information indicating past surgical complications associated with a health professional in conjunction with the planned surgical procedure;
    selecting a video of a surgical procedure from a plurality of videos of surgical procedures based on the past surgical complications;
    obtaining, based on analysis of the video to identify intraoperative events appearing in the video, a plurality of time points corresponding to a plurality of key intraoperative events in the video;
    obtaining at least one property of the plurality of key intraoperative events, wherein obtaining at least a part of the at least one property of the plurality of key intraoperative events includes analyzing the video;
    visually presenting the at least one property of the plurality of key intraoperative events to a user;
    in response to the visual presentation, receiving from the user a selection of a selected intraoperative event of the plurality of key intraoperative events, the selected intraoperative event depicting a leak;
    analyzing the video to identify a source of the leak; and
    in response to receiving the selection of the intraoperative event, presenting at least part of at least one frame of the video associated with a time point of the plurality of time points corresponding to the selected key intraoperative event, and the identified source of the leak.

2. The method of claim 1, further comprising:
    analyzing the video to identify at least part of the plurality of time points corresponding to a plurality of key intraoperative events; and
    analyzing the video to identify at least part of the at least one property of the plurality of key intraoperative events.

3. The method of claim 1, further comprising:
    obtaining an electronic health record associated with the video of the surgical procedure; and
    analyzing textual information from the electronic health record to identify at least part of the at least one property of the plurality of key intraoperative events.

4. The method of claim 1, wherein the plurality of key intraoperative events comprises a plurality of intraoperative phases.

5. The method of claim 1, wherein the plurality of key intraoperative events comprises at least one of an insertion, a removal, or a usage of medical equipment.

6. The method of claim 1, wherein the plurality of key intraoperative events comprises an intraoperative surgical error.

7. The method of claim 1, wherein the obtained information further comprises information related to a patient, and wherein the selection of the video is based on the information related to the patient.

8. The method of claim 1, wherein the obtained information further comprises information related to a second health professional, and wherein the selection of the video is further based on the information related to the second health professional.

9. The method of claim 1, wherein the obtained information comprises information related to past performance of the health professional, and the selection of the video is based on the past performance.

10. The method of claim 1, wherein the obtained information further comprises information related to an intraoperative surgical error, and wherein the selection of the video is based on the information related to the intraoperative surgical error.

11. The method of claim 1, wherein the obtained information further comprises information related to an intraoperative event, and wherein the selection of the video is based on the information related to the intraoperative event.

12. The method of claim 1, wherein the obtained information further comprises information related to a second video of a second surgical procedure, and wherein the selection of the video is based on the information related to the second video.

13. The method of claim 1, further comprising presenting, in conjunction with the at least one frame, at least one property of the selected intraoperative event.

14. The method of claim 13, wherein the selected intraoperative event further comprises a bleeding, the method further comprising analyzing the video to identify an amount associated with the bleeding, and the presented at least one property comprises the identified amount.

15. The method of claim 13, wherein the presented at least one property comprises the identified source of the leak.

16. The method of claim 13, wherein the selected intraoperative event further comprises an injury, the method further comprising analyzing the video to identify a type of the injury, and the presented at least one property comprises the identified type.

17. The method of claim 1, further comprising:
analyzing the at least one frame to detect a region of the at least one frame depicting the selected intraoperative event; and
based on the detected region, present an overlay over the presentation of the at least part of at least one frame.

18. The method of claim 1, further comprising presenting, in conjunction with the at least one frame, information related to complications associated with the selected intraoperative event.

19. The method of claim 1, further comprising presenting, in conjunction with the at least one frame, suggestion of at least one additional video.

20. The method of claim 1, wherein the receiving from the user the selection of the selected intraoperative event includes receipt of a time point corresponding to a video frame at a start of the intraoperative event.

21. The method of claim 1, wherein the obtained information further comprises information related to a surgical instrument associated with the planned surgical procedure, and the selection of the video is further based on the surgical instrument.

22. A system for presentation of videos of surgical procedures, the system comprising:
at least one processor configured to:
obtain information related to a planned surgical procedure, the information indicating past surgical complications associated with a health professional in conjunction with the planned surgical procedure;
select a video of a surgical procedure from a plurality of videos of surgical procedures based on the past surgical complications
obtain, based on analysis of the video to identify intraoperative events appearing in the video, a plurality of time points corresponding to a plurality of key intraoperative events;
obtain at least one property of the plurality of key intraoperative events, wherein obtaining at least a part of the at least one property of the plurality of key intraoperative events includes analyzing the video;
visually present the at least one property of the plurality of key intraoperative events to a user;
in response to the visual presentation, receive from the user a selection of a selected intraoperative event of the plurality of key intraoperative events, the selected intraoperative event depicting a leak;
analyzing the video to identify a source of the leak; and
in response to receiving the selection of the intraoperative event, present at least one frame of the video associated with a time point of the plurality of time points corresponding to the selected key intraoperative event, and the identified source of the leak.

23. A non-transitory computer readable medium storing data and computer implementable instructions for carrying out a method for presentation of videos of surgical procedures, the method comprising:
obtaining information related to a planned surgical procedure, the information indicating past surgical complications associated with a health professional in conjunction with the planned surgical procedure;
selecting a video of a surgical procedure from a plurality of videos of surgical procedures based on the past surgical complications;
obtaining, based on analysis of the video to identify intraoperative events appearing in the video, a plurality of time points corresponding to a plurality of key intraoperative events;
obtaining at least one property of the plurality of key intraoperative events, wherein obtaining at least a part of the at least one property of the plurality of key intraoperative events includes analyzing the video;
visually presenting the at least one property of the plurality of key intraoperative events to a user;
in response to the visual presentation, receiving from the user a selection of a selected intraoperative event of the plurality of key intraoperative events, the selected intraoperative event depicting a leak;
analyzing the video to identify a source of the leak; and
in response to receiving the selection of the intraoperative event, presenting at least one frame of the video associated with a time point of the plurality of time points corresponding to the selected key intraoperative event, and the identified source of the leak.

* * * * *